United States Patent [19]

Timson

[11] 4,302,108

[45] Nov. 24, 1981

[54] DETECTION OF SUBSURFACE DEFECTS BY REFLECTION INTERFERENCE

[75] Inventor: William J. Timson, Belmont, Mass.

[73] Assignee: Polaroid Corporation, Cambridge, Mass.

[21] Appl. No.: 7,011

[22] Filed: Jan. 29, 1979

[51] Int. Cl.³ .................... G01B 11/00; G01N 21/84; G01J 1/00
[52] U.S. Cl. .................................. 356/359; 356/431; 250/341; 250/359
[58] Field of Search ............... 356/352, 357, 359, 430, 356/431; 250/340, 341, 359

[56] References Cited

U.S. PATENT DOCUMENTS

| | | |
|---|---|---|
| 3,026,415 | 3/1962 | Lake, Jr. et al. |
| 3,206,603 | 9/1965 | Mauro .................................. 250/341 |
| 3,325,649 | 6/1967 | Bird ..................................... 250/341 |
| 3,556,664 | 1/1971 | Blaisdell et al. |
| 3,589,817 | 6/1971 | Sugaya . |
| 3,646,353 | 2/1972 | Bhullar et al. |
| 3,693,025 | 9/1972 | Brunton .............................. 250/340 |
| 3,734,624 | 5/1973 | Cornelius ........................... 356/431 |
| 3,748,047 | 7/1973 | Millgard et al. |
| 3,858,981 | 1/1975 | Jaerisch et al. ..................... 356/359 |
| 3,994,586 | 11/1976 | Sharkins et al. |

FOREIGN PATENT DOCUMENTS 880135 10/1961 United Kingdom ................ 356/431

Primary Examiner—Alfred E. Smith
Assistant Examiner—Janice A. Howell
Attorney, Agent, or Firm—John W. Ericson

[57] ABSTRACT

A process for detecting defects in a multiply layered light transmitting structure, comprising illuminating the surface of the structure with a beam of light at an angle of incidence to the structure at which at least a portion of the beam will be reflected, and detecting the intensity of the reflected beam to locate subsurface as well as surface anomalies in the structure.

14 Claims, 8 Drawing Figures

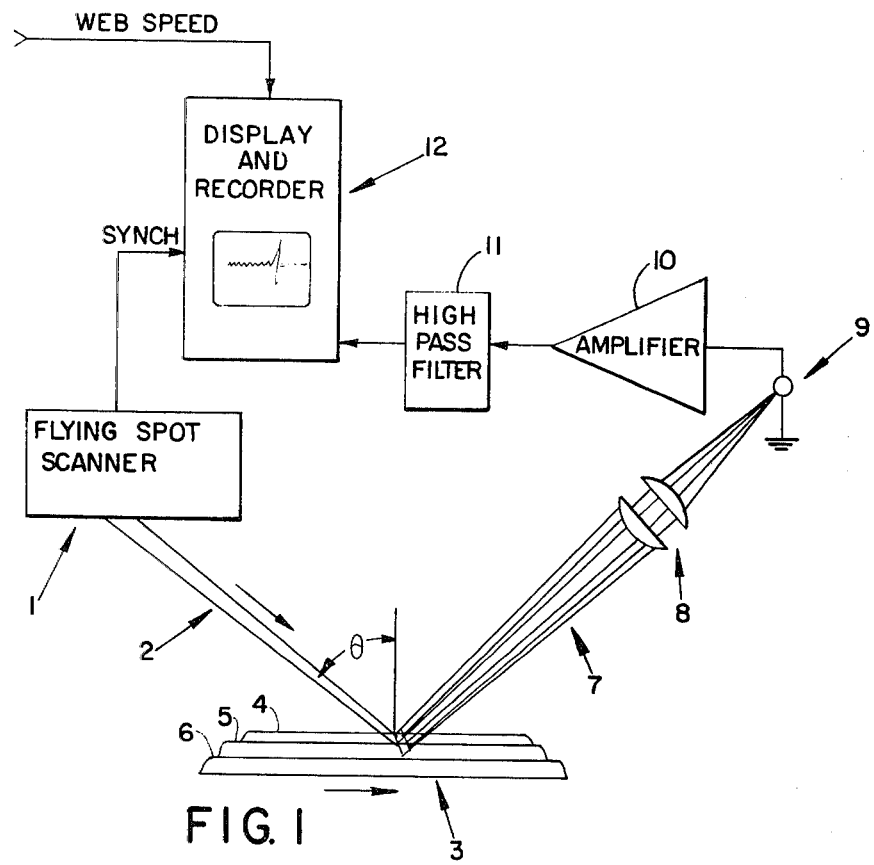
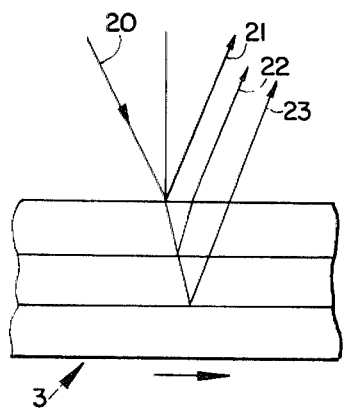
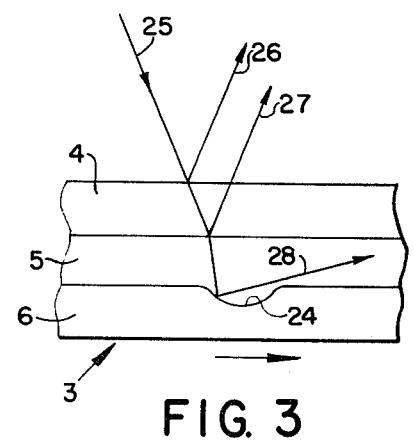

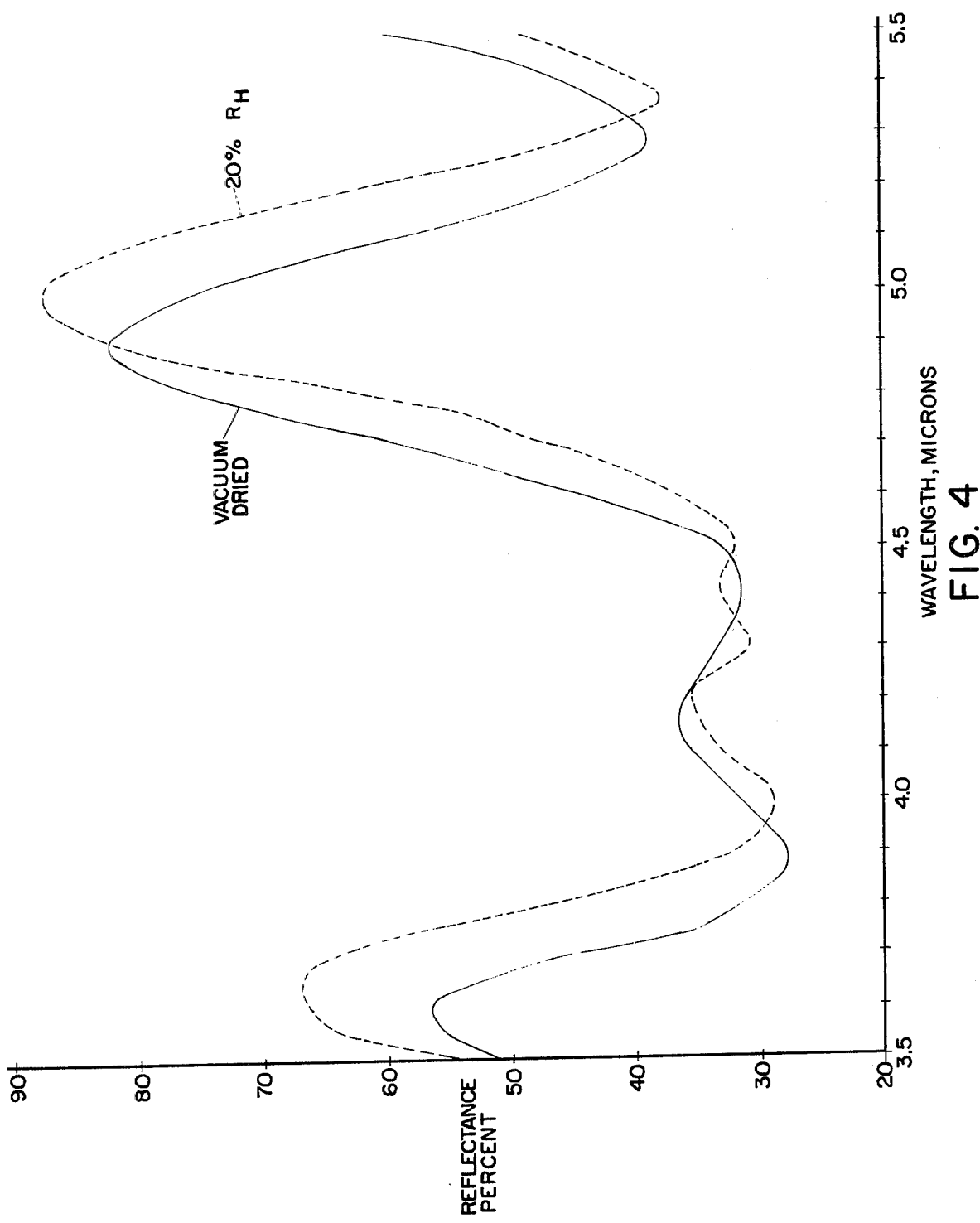

DETECTION OF SUBSURFACE DEFECTS BY REFLECTION INTERFERENCE

BACKGROUND OF THE INVENTION

This application relates to the inspection of multiply layered light transmissive structures, and particularly to a novel method for detecting defects beneath the surfaces of such structures.

The usual processes for the inspection of products such as photographic film and the like for defects consist primarily of inspection for surface defects, as by the use of a flying spot scanner and a reflection or transmission detector. U.S. Pat. No. 3,026,415 shows apparatus for detecting defects on webs such as photographic film comprising a flying spot scanner, and describes circuits for processing the signals from the scanner to eliminate noise and characterize particular defects. In this patent, the usual preference for the use of light of a wave length that will not affect the film being inspected is indicated. Other patents of interest in connection with the flying spot scanning of webs for defects are U.S. Pat. Nos. 3,589,817; 3,646,353 ; and 3,748,047.

In U.S. Pat. No. 3,556,664, it is stated that, particularly for colored film and like products, the use of infrared light, to which the emulsions will not respond, is not adequate to reveal subsurface defects by transmission methods. Instead it is proposed to use actinic light at a sufficiently low exposure level that the reciprocity failure characteristics of the emulsions will prevent damage during inspection.

Another approach to the use of visible light for defect detection is described in U.S. Pat. No. 3,734,624. A flying spot scanner is provided in which the flying beam is polarized so that essentially all of the beam will be reflected from the web being inspected upon illumination at a grazing angle of incidence. In this way, visible light can be used for inspection without any penetration of light into the emulsion that would expose the emulsion.

U.S. Pat. No. 3,994,586 discusses a method of measuring the thickness and uniformity of a translucent film by the detection of differences in intensity between a first beam of light at an infrared frequency which is not absorbed by the film material, and a second beam of light that is selectively absorbed by the material. This patent is directed to a problem encountered in conventional reflectance measurements, which is caused by interference between a portion of the illuminating beam falling on the surface and reflected therefrom, and a residual portion of the beam that passes through the material and is reflected from the next surface below, providing an interfering difference in path length. The patent proposes polarizing techniques for removing the unwanted component from a reflected beam to prevent such reflectance interference signals.

So far as is known, prior to the present invention, the only method proposed for detecting subsurface defects in photographic film is that disclosed in the above-cited U.S. Pat. No. 3,556,664, using light transmitted through the emulsions. This method requires very low exposure levels, and correspondingly reduced sensitivity. Moreover, it is inapplicable to opaque film structures, such as those incorporating subtractive dye systems, or those having an opaque base. The object of this invention is to facilitate the detection of subsurface defects in structures such as color films and the like, which can be employed even with structures that will not permit the passage of light throughout the structure, but only through one or more layers.

Briefly, the above and other objects of the invention are attained by a process in which a multilayered web is illuminated by a beam of light that is partially reflected and partially transmitted through each of the several layers of the structure. The reflected beam is focused on a detector, producing a combined reflectance interference signal. This signal is a function of the thicknesses and indices of refraction of the several layers and of the light scattering and light absorbing properties thereof. It has been found that signals produced in this manner will indicate even very small subsurface defects, such as bubbles, streaks and the like, which may occur. Infrared light, to which emulsions are insensitive, may be used. Thus, a much more intense beam can be used than could be tolerated with methods employing visible light. Preferably, the web is moved in one direction while the beam is moved across it in a perpendicular direction by a flying spot scanner.

The invention will best be understood in the light of the following detailed description, together with the accompanying drawings.

In the drawings,

FIG. 1 is a fragmentary schematic diagram illustrating the use of a flying spot scanner to detect subsurface defects in a moving multilayered web in accordance with the invention;

FIG. 2 is a schematic diagram illustrating several of the reflected rays produced by a single ray incident on the multilayered web of FIG. 1;

FIG. 3 is a schematic diagram similar to FIG. 2 but illustrating an aberrant reflected ray produced by a defect in the web;

FIG. 4 is a graph of reflectance versus wavelength of a nine-layered negative structure under two conditions of moisture content;

Figure 5:
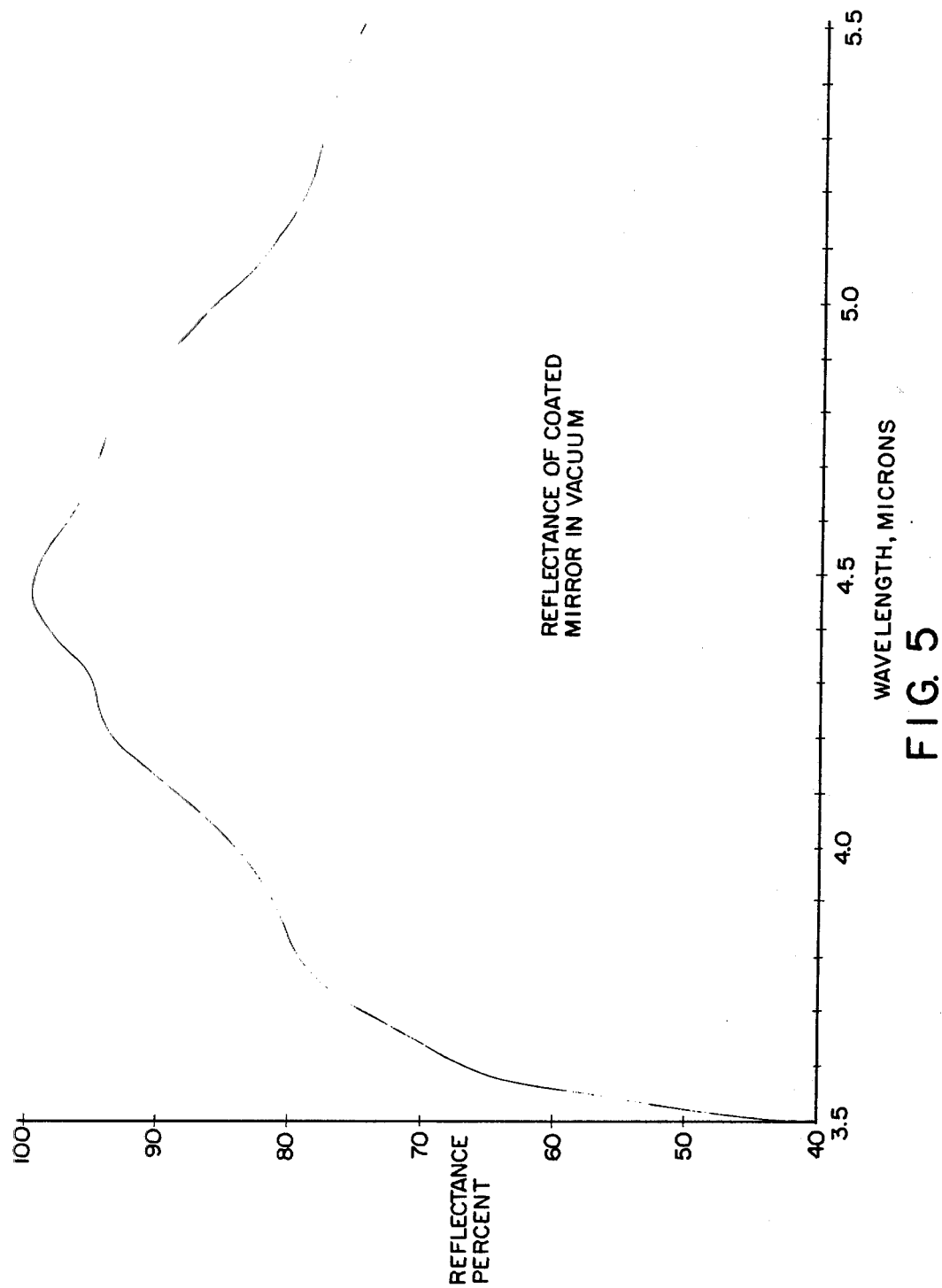
FIG. 5 is a graph of reflectance versus wavelength of a mirror coated with a layer comprising a mixture of the compositive of the nine layers of the negative used to produce the data of FIG. 4.

FIG. 1 shows a conventional flying spot scanner 1, such as those described in the above cited patents, arranged to produce a beam of infrared light 2 and to cause the beam to scan in directions perpendicular to the plane of the drawing across a multiply layered web generally designated 3.

The light source employed in the flying spot scanner is preferably a laser. Preferred operating wavelengths are in the range of from 2 to 6 microns for photosensitive layered materials in which the individual layers are less than 50 microns in thickness. For use with layered materials that are relatively insensitive to radiation, any desired wavelength appropriate to the layer geometry may be employed.

The scanning beam 3 may be unpolarized, but is preferably plane polarized, and most preferably polarized in planes perpendicular to the plane of incidence, although light polarized in planes parallel to the plane of incidence will also give useful results at angles sufficiently removed from Brewster's angle so that a useful portion is reflected. Brewster's angle $\beta$ is given by $\beta = \arctan n$, where n is the index of refraction of the top layer at the wavelength of the light source. At Brewster's angle, the parallel polarized beam is almost totally absorbed. For many materials of interest, Brewster's angle will be between 52 and 62 degrees.

The beam 3 is preferably focused to a very small spot at the point of incidence on the web, although a narrow collimated beam can be employed if so desired. The spot size is greatly exaggerated in FIG. 1 to indicate the behavior of typical rays.

The web 3 comprises a plurality of layers such as 4 and 5 on a base 6. The web 3 is assumed to be moving in the direction shown by the arrow at a speed selected in dependence on the transverse scanning speed so that a desired resolution is attained.

At least the layers 4 and 5 of the web 3 are assumed to transmit and to reflect portions of an incident beam of light in the infrared region. Thus, a portion of each incident ray is reflected from the surface of the layer 4, another portion is refracted by the layer 4 and reflected from the surface of the layer 5, and still another portion is refracted by the layer 5 and reflected from the surface of the support 6. The result of these and other reflections and re-reflections will be a reflected bundle of rays 7 containing components shifted in phase and amplitude in a manner determined by the materials and thicknesses of the layers 4 and 5 and the support 6.

The support 6 may be transparent, translucent, or opaque, and thus may transmit or absorb more or less of the light that does not appear in the bundle 7.

Light comprising the reflected bundle 7 is focused by an apropriate optical system schematically indicated at 8 onto a photodetector 9, such as an indium-antimony photovoltaic detector. The signal from the detector 9 is amplified by an amplifier 10, and applied to a high pass filter 11 in which slowly varying components characteristic of the response of the system in the absence of a defect are discarded.

The output of the filter 11 is applied to any desired conventional display and/or recording system 12, which may comprise an oscilloscope synchronized with the flying spot scanner 1 for directly indicating the presence of a defect by an abrupt change in the signal produced by the detector 9. Alternatively, or in addition, the system 12 may comprise a recorder of any conventional design, to which a web speed (or position) signal is applied by conventional means sensing the speed or position of the web 3 so that the position of a detected defect in the web can be recorded.

The process of defect detection in accordance with the invention depends on relatively high frequency transitions in the signal produced by the photodetector 9 in response to anomalies in the structure of the layered web 3. The several components of the reflected bundle of rays 7 will differ in amplitude, and will differ in phase by amounts depending on the differences in path length for the rays reflected and scattered from the several surfaces of the translucent layers such as 4 and 5 on the web 3. The relative amplitude of the components reflected from the several layers will also fluctuate as a function of selective absorption in a manner to be discussed in more detail below. Where the layers are of uniform thickness, these effects will result in a signal at the detector 9 which would ideally be of constant amplitude. However, in practice the signal produced when scanning uniform material may contain spurious components of relatively low frequency, which are removed by the filter 11.

FIG. 2 is a simplified diagram illustrating the scanning of a uniform portion of the web 3. For clarity, a single incident ray 20 is shown, portions of which are refracted and reflected to form three rays 21, 22 and 23 comprising a portion of the bundle 7 in FIG. 1. These reflected rays will have relative phases and amplitudes determined by the thicknesses, indices of refraction, and absorption characteristics of the layers 4 and 5, causing the detector 9 to produce a corresponding signal amplitude.

FIG. 3 illustrates the scanning of a portion of the web 3 containing an anomaly 24, shown as a valley in the layer 6 filled by material of which the layer 5 is made. As shown, an incident ray 25 at the same angle of incidence as the ray 20 produces reflected components 26 and 27 identical to the components 21 and 22. However, the component 28 is reflected in the valley 24, so that it may not appear in the reflected bundles received by the detector, or if it does, will be altered in phase. The signal produced by the detector 9 will thus abruptly change in amplitude as the scanning beam reaches the anomaly 24, then return to the amplitude produced as suggested in FIG. 2.

The behavior of the bundle of rays 7 in FIG. 1 is obviously very much more complicated than that just described. The fact that a useful and sensitive defect detection signal may be obtained will best be understood in the light of the following more detailed discussion.

FIG. 4 shows reflectance spectra made with a fourier transform interferometric infrared spectrometer on a beam of infrared light refracted at an angle of about 40° from a sample of the negative used in Polaroid SX-70 film units. The beam was polarized in planes perpendicular to the plane of incidence on the web.

The negative comprised nine optically transmissive layers on an opaque polyester base. The total thickness of the nine layers was about 13 microns. Three of these layers comprised photosensitive silver halide emulsions, and these layers were interspersed with dye developer layers. The outer dye developer layer absorbed blue light, the next inner dye developer layer absorbed green light, and the third dye developer layer absorbed red light, so that all visible light would be absorbed in passing through the three dye developer layers. However, the nine layers were all relatively transparent to infrared light.

FIG. 4 shows the reflectance in percent of the reflectance that would be measured by the instrument with light reflected from an aluminum mirror, over the range from 3.5 to 5.5 microns, under two conditions of moisture content. In FIG. 4, the dashed curve represents data from the negative in equilibrium with air at a relative humidity of twenty percent. The curve in solid line was made from the same negative after vacuum drying.

The curves in FIG. 4 are not known to be susceptible to quantitative analysis. Among other things, the fact that there are nine optically transmissive layers in the negative, each of different chemical composition, discourages any attempt at a formal analysis. Several basic mechanisms are clearly involved to some degree in the reflectance spectra; these include absorption of light in the various layers of the negative, interference of light reflected from the several layers, and scattering by silver halide crystals in the emulsion layers. Of these mechanisms, any might conceivably account for one of the reflectance spectra shown in FIG. 4. However, the shift in the two curves indicates that interference effects contribute substantially.

More specifically, the maxima and minima in the curves of FIG. 4 suggest constructive and destructive interference effects, which are a strong function of wavelength as is the reflectance in FIG. 4. Further, the negative in equilibrium with air at 20 percent relative humidity contained roughly 10 to 15 percent of water by weight, whereas the vacuum dried negative would contain only from 0 to about 5 percent. This represents a change in thickness on the order of about 10 percent. If the curves in FIG. 4 represent interference phenomena, one would expect the maxima and minima in the curve for the thinner vacuum dried negative to occur at shorter wavelengths than for the air dried negative. And the shift in the curves is indeed in this direction. For example, the maximum at about 5 microns for the air-dried negative corresponds to a maximum at around 4.8 microns for the vacuum dried negative. Similarly, the minimum at around 5.38 microns for the air dried negative corresponds to a minimum of about 5.28 microns for the vacuum dried negative.

FIG. 5 shows a reflection spectrum for an aluminum mirror coated with a single layer made by mixing the coating compositions used to make the SX-70 negative, in the same amounts and proportions, and drying to form a single coated layer with the same thickness as the nine layers of the negative, and with the same composition as the total composition of the nine layers of the negative. It will be seen that this spectrum is relatively featureless over the range of 3.5 to 5.5 microns. This graph was made with data taken in the same manner as discussed above in connection with FIG. 4, and indicates that the curves of FIG. 4 represent predominantly interference effects, and not the effects of selective infrared absorption phenomena.

Figure 6:
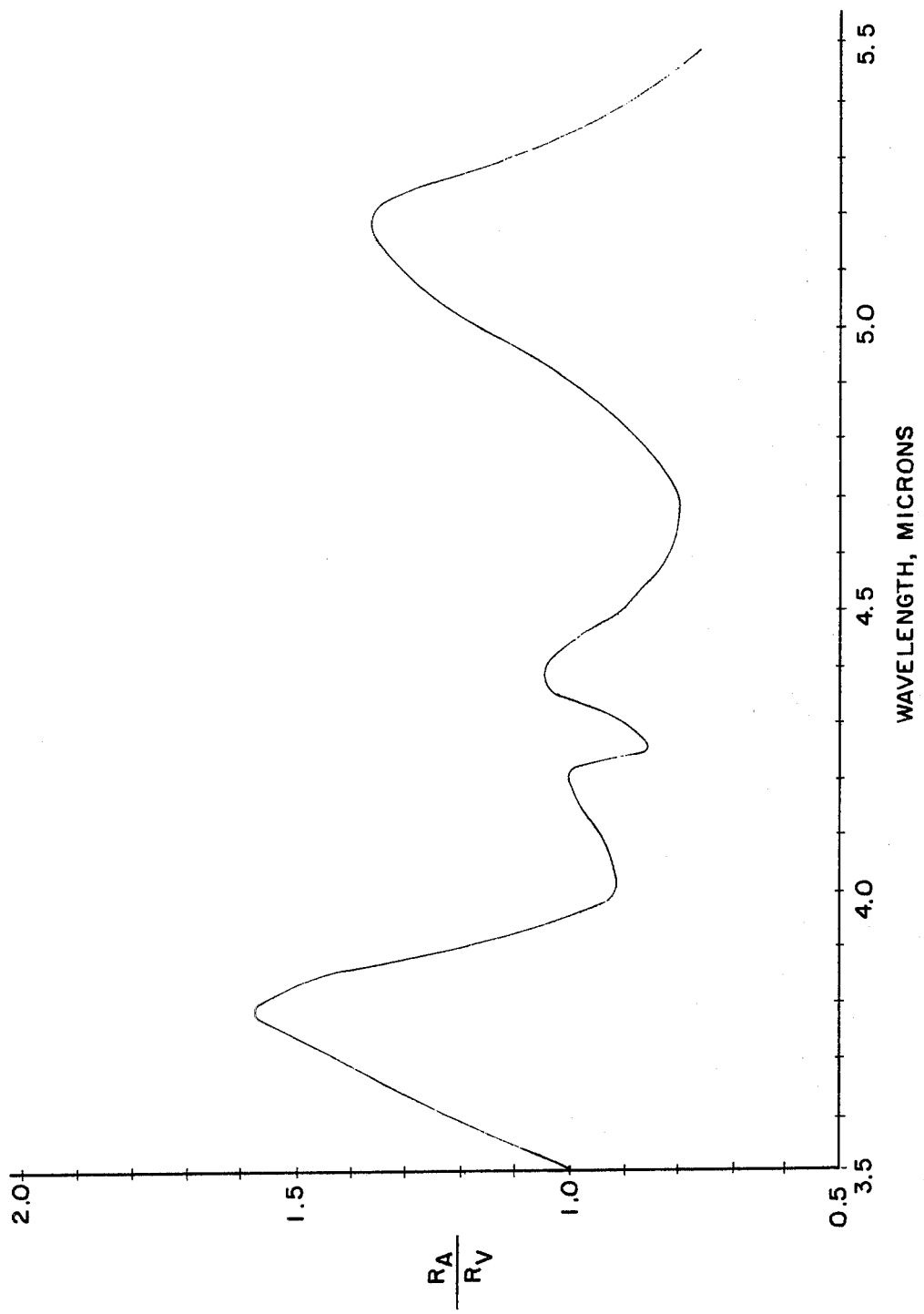
FIG. 6 is a graph of the ratio of the reflectances of the nine-layered negative used to produce the data of FIG. 4 under two conditions of moisture content versus wavelength.

FIG. 6 is a graph of the ratio of the reflectance Ra of the air dried negative divided by the reflectance Rv of the vacuum dried negative, as a function of wavelength, made from the data of FIG. 4. This ratio is a measure of the sensitivity of the reflectance signal to changes in thickness, and serves as an indication of optimum wavelengths for use in defect detection. In particular, the peaks at about 3.8 and 5.2 microns indicate that these wavelengths would be good choices for defect detection. Note that these wavelengths do not coincide with maxima or minima in FIG. 4 but are in regions where the curves of FIG. 4 have high slopes.

Figure 7:
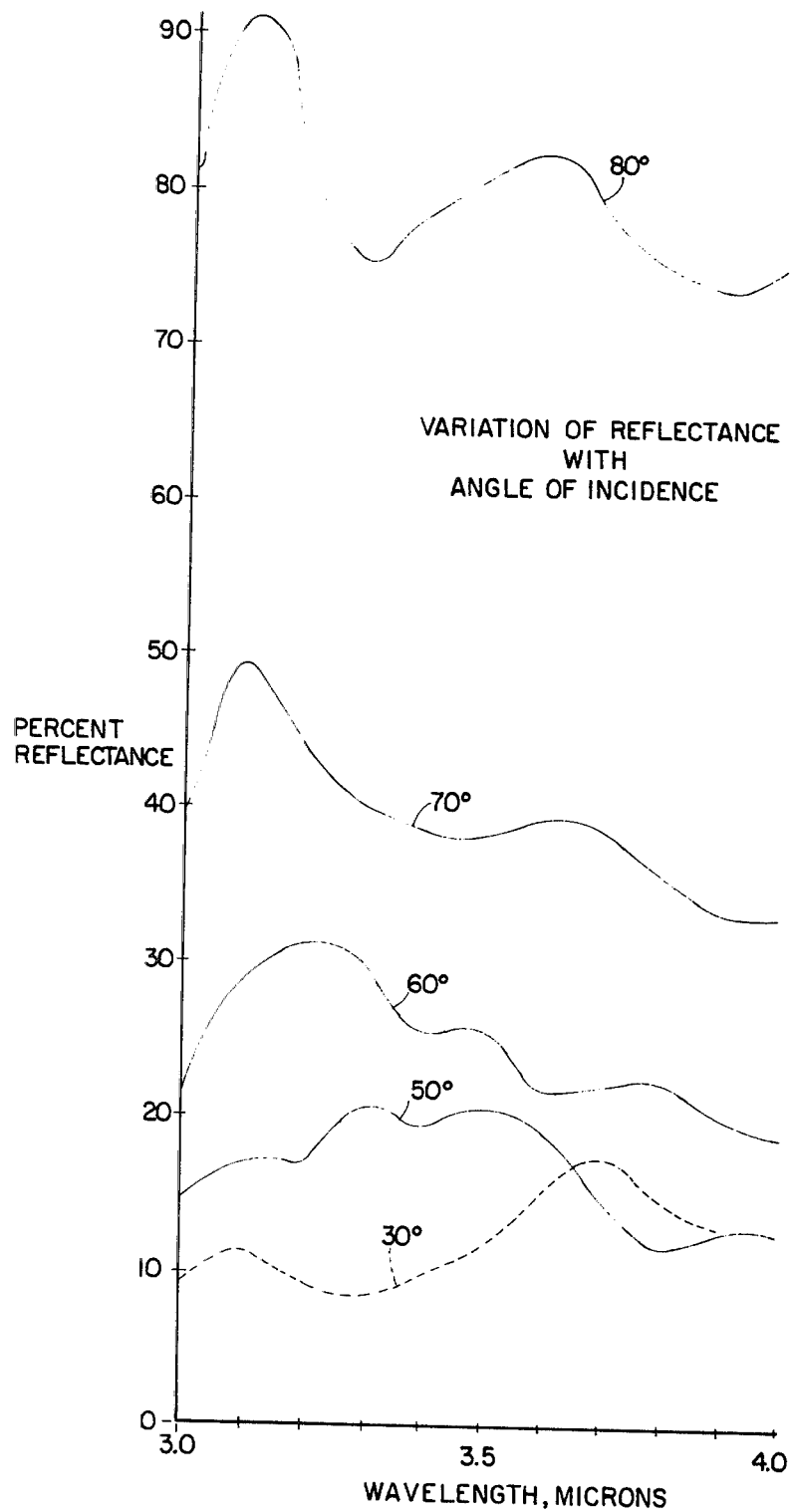
FIG. 7 is a graph of reflectance versus wavelength for a nine-layered negative such as that used to produce the data of FIG. 4 at various angles of incidence.

FIG. 7 shows reflectance spectra similar to those in FIG. 4, but with the scanning beam at various angles of incidence to the negative. The angles of incidence are relative to the normal. As would be expected, a greater percentage of light is reflected at a larger angle of incidence. Thus, a stronger signal is available at higher angles of incidence. However, it has been found that the signal-to-noise ratio is larger at smaller angles of incidence, so that angles in the range of 30° to 50° are preferred, although the angle of incidence is not critical.

A significant feature of the curves in FIG. 7 is that the maxima in the curves shift generally toward longer wavelengths at lower angles of incidence. The fact that the reflection interferences peaks shift only gradually with changes in the angle of incidence is a distinct advantage. This is that a stable reflection interference signal can be obtained despite slight changes in the angle of incidence that might be introduced by the scanner.

The fact that the peaks do shift makes it possible to make optimum use of a light source at a particular wavelength, by choosing an angle of incidence at which the reflection signal is most sensitive to changes in the structure of the layered web at that wavelength. For example, if it was desired to employ a laser operating at 5.3 microns in the sensitive region indicated in FIG. 6 to occur at 5.2 microns at a 40° angle of incidence, one could simply decrease the angle of incidence enough to move the most sensitive region to 5.3 microns.

Figure 8:
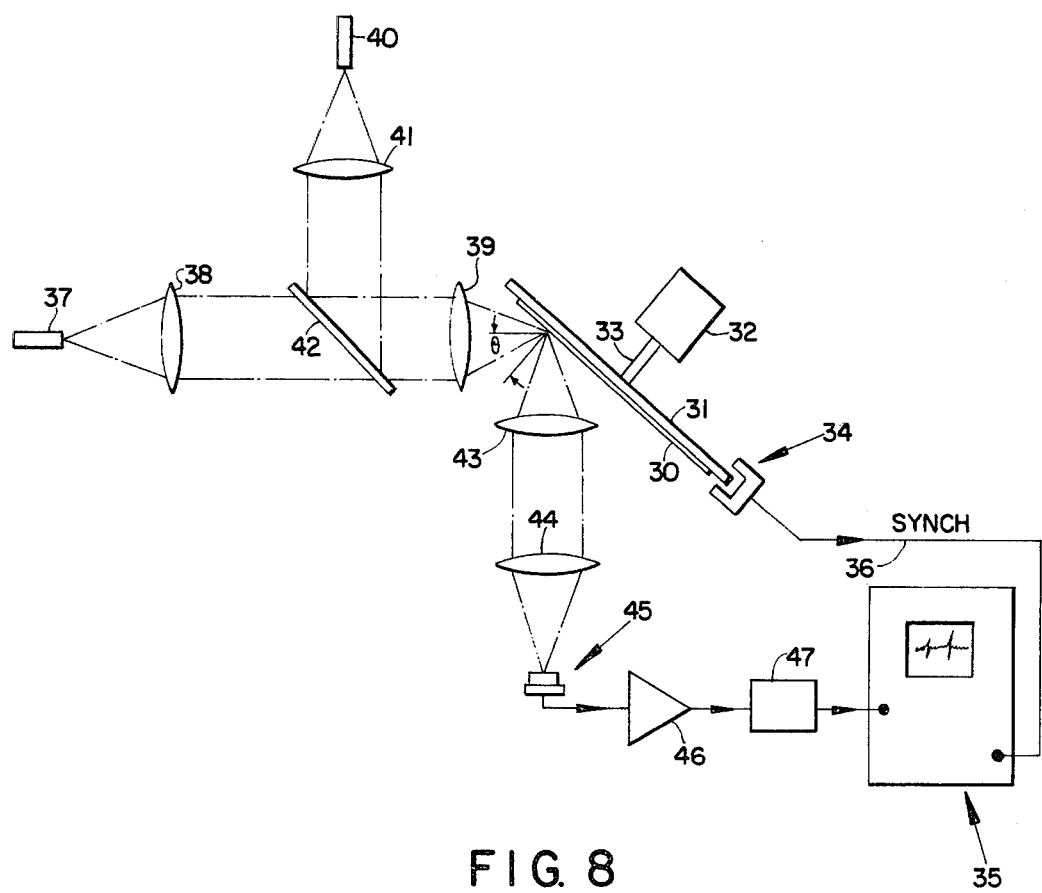
FIG. 8 is a schematic block and wiring diagram of apparatus useful in obtaining design data for use in the practice of the invention.

FIG. 8 shows apparatus useful in establishing the operating parameters for use in applying the process of the invention to specific defect detection problems. Generally, the apparatus comprises a fixed spot scanner for repetitively scanning a region of a multilayer sample 30 mounted on a disc 31 that is rotated at constant speed by a motor 32 having an output shaft 33 fixed to the disc 31.

The disc 31 is notched or otherwise marked at its periphery to cooperate with a shaft angle generator schematically indicated at 34 to produce synchronizing signals marking the beginning of each revolution of the disc 31, and thus enable the location of the angle of a defect in the sample 30 relative to a reference radius on the disc. The shaft angle generator may comprise a light emitting diode and a detector arranged in an optical path that is blocked by the edge of the disc except in the area of the slot. The synchronizing pulses so produced are applied to the external synchronizing input terminal of a conventional oscilloscope 35 as indicated by the lead 36.

The optical scanning system in FIG. 8 comprises a first laser 37 operating at a selected wavelength for defect detection. Light from the laser 37 is collimated by a lens 38 and focused to a small spot on the sample 30 by a lens 39.

When the operating wavelength of the laser 37 is outside of the visible range, a second laser 40 is preferably provided that has an output beam in the visible range. Light from the laser 40 is collimated by a lens 41. Portions of the collimated beams from the lasers 37 and 40 are brought into the same optical axis by a beam splitter 42. This arrangement facilitates visual inspection of the location of the scanning spot on the sample.

Light reflected from the sample 30 is collected by a lens 43 and focused by a lens 44 onto a suitable photodetector 45. The signal from the photodetector 45 is supplied to an amplifier 46. The output of the amplifier 46 is applied to a filter 47, and the output of the filter 47 is applied to the vertical input terminal of the oscilloscope 35.

As noted above, a high pass filter is preferred for the detection of small defects in thin multilayered material such as a photographic film. However, for gross defects, or to measure gradual variations in film thickness caused by non-uniform coating, a low pass filter may be preferred, and to concentrate on a particular class of defects, a band pass filter may be the best choice. The apparatus of FIG. 8 facilitates the choice of the pass band for the filter 47 by making it possible to compare the responses of different filters to the same defects.

In using the apparatus of FIG. 8 to detect defects in a sample 30 of photographic color negative, the following components and operating parameters were employed. The laser 37 was a diode laser rated at about 1.22 milliwatts and had an operating wavelength of 5.3 microns. The laser 40 was a helium neon laser operating at a wavelength of 633 nanometers. The disc 31 was rotated at 20 revolutions per second, and the available radius for observation on the negative sample 30 was from 0 to 1 inch. The angle of incidence $\theta$ in FIG. 2 was 45°, and the scanning beam was polarized perpendicular to the plane of incidence. The filter 47 was a high pass filter having a selectable roll-on frequency. Among the subsurface defects detected were bubbles, streaks, and fan-shaped marks following bubbles. In many instances these defects were invisible or very faintly visible to the naked eye; in general, they were 100 microns in size or larger. However, granularity in relatively coarse-grained negative material was also detected.

The scanning speed of the scanning spot relative to the sample in the apparatus of FIG. 8 when the disc was rotated at 20 rps would be 159.6 centimeters per second at a radius of 0.5 in. or 1.27 cm. The primary factors limiting scanning speed are the speed at which the scanner can move the scanning spot over the web, the response time of the detector, and the gain-bandwidth product of the amplifier and detection system. The power of the scanning laser should be adequate to achieve a useful signal-to-noise ratio at the selected scanning speed.

As used herein, the angle of incidence is the angle between an incident ray and the normal to the surface on which the ray is incident. The plane of incidence is that plane containing an incident ray and the normal to the surface on which the ray is incident. As applied to a flying spot scanner, in which the angle of incidence does not change during the scan, but the plane of incidence does change, the plane of incidence means the plane at any instant in the scan. It will be recognized that if light is polarized in planes perpendicular to the plane of incidence of the scanning beam at one instant during the scan, it will also be polarized perpendicular to the plane of incidence at any other instant during the scan.

While the invention has been described with respect to the details of specific illustrative practices and apparatus, many changes and variations will occur to those skilled in the art upon reading this description, and such can obviously be made without departing from the scope of the invention.

Having thus described the invention, what is claimed is:

1. The method of inspecting a layered material having at least one optically transmissive surface layer and at least one other layer adjacent said optically transmissive layer comprising the steps of moving said material past an inspection station, directing a beam of light onto said optically transmissive surface layer at an acute angle of incidence, focusing light reflected and scattered from said material onto intensity detecting means to produce a reflection interference signal determined by the relative phases and amplitudes of the reflected and scattered components of said beam, and detecting changes in said signal produced in the presence of anomalies in one or more of said layers.

2. The method of claim 1, in which said beam is repetitively swept across said moving material in a direction normal to the direction of its motion past said inspection station.

3. The method of claim 2, further comprising the step of polarizing said light in planes perpendicular to the planes of incidence of said beam on said material.

4. The method of claim 2, further comprising the step of polarizing said beam in planes parallel to the plane of incidence of said beam on said material.

5. The method of claim 1, in which said angle of incidence and the wavelength of said light are chosen in a region in which said signal changes rapidly with wavelength.

6. The method of inspecting a multiply coated color negative comprising a plurality of photosensitive layers interspersed with dye layers comprising a set of dyes which together will absorb all light in the visible spectrum and transmit at least a portion of infrared light, said layers being coated on an opaque base sheet, comprising the steps of moving said negative past an inspection station, directing a beam of infrared light at the coated layers on said base sheet, focusing infrared light reflected and scattered from said layers onto a photodetector to produce a reflection interference signal determined by the relative phases and amplitudes of the reflected and scattered components of said beam, monitoring the position of said beam on said negative, and registering abrupt changes of said signal as a function of the position of said beam on said negative.

7. The method of claim 6, in which the wavelength of said light is between 2 and 6 microns.

8. The method of claim 6, in which said beam is directed at said coated layers by a flying spot scanner scanning said negative in a direction normal to the direction of movement of said negative past said inspection station.

9. The method of claim 8, further comprising the step of polarizing said beam of light in planes parallel to the planes of incidence of said beam on said negative.

10. The method of inspecting a web comprising a plurality of layers on a base sheet, at least an outer set of said layers being at least partially transmissive to light of at least one wavelength, comprising the steps of moving said web past an inspection station, scanning said web with a flying spot of light at a wavelength at which said set of layers is at least partially transmissive, said flying spot being formed by a beam of light directed onto said layers at an acute angle of incidence, collecting light reflected and scattered from said layers, focusing said collected light on a photodetector to produce a reflectance interference signal determined by the relative phases and amplitudes of the reflected and scattered components of said beam, and detecting abrupt changes in said signal produced by anomalies in said layers.

11. The method of claim 10, in which said flying spot is polarized in planes perpendicular to the plane of incidence of said beam on said web.

12. The method of claim 10, in which said flying spot is polarized in planes parallel to the planes of incidence of said beam on said web.

13. The method of claim 10, further comprising the steps of registering the position of said spot on said web, and recording abrupt changes in said signal as a function of said position.

14. The method of claim 10, in which the angle of incidence of said beam and the wavelength of said light are chosen in a region in which said signal changes rapidly with wavelength.

* * * * *